United States Patent
Eriksson et al.

(10) Patent No.: US 9,795,909 B2
(45) Date of Patent: Oct. 24, 2017

(54) GAS EXHAUST FILTER DEVICE FOR A BIOREACTOR

(75) Inventors: Henrik K. Eriksson, Alunda (SE); Patric Fricking, Uppsala (SE); L. Johan Carlsson, Kungsangen (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 426 days.

(21) Appl. No.: 14/241,550

(22) PCT Filed: Aug. 29, 2012

(86) PCT No.: PCT/SE2012/050912
§ 371 (c)(1),
(2), (4) Date: Feb. 27, 2014

(87) PCT Pub. No.: WO2013/032392
PCT Pub. Date: Mar. 7, 2013

(65) Prior Publication Data
US 2014/0193883 A1    Jul. 10, 2014

(30) Foreign Application Priority Data
Aug. 31, 2011    (SE) ...................................... 1150790

(51) Int. Cl.
*B01D 46/00* (2006.01)
*B01D 46/52* (2006.01)
*C12M 1/12* (2006.01)
*C12M 1/00* (2006.01)

(52) U.S. Cl.
CPC ....... *B01D 46/0039* (2013.01); *B01D 46/521* (2013.01); *C12M 29/04* (2013.01); *C12M 37/02* (2013.01)

(58) Field of Classification Search
CPC ........ B01D 46/10; B01D 45/00; B01D 46/30; B01D 45/08; B01D 53/04; B01D 50/00; F02M 25/08; F02M 35/022; F02M 35/02
See application file for complete search history.

(56) References Cited

U.S. PATENT DOCUMENTS 3,992,177 A    11/1976  Welteroth
4,007,026 A *  2/1977   Groh ....................... A47L 9/127
                                                                15/348
(Continued)

FOREIGN PATENT DOCUMENTS

DE       102008027638       12/2009
EP       135488        *    3/1985   ............. B01D 45/06
(Continued)

OTHER PUBLICATIONS

Stadler, E., et al., Pharmaceutical Engineering, May/Jun. 2010, p. 42-52.
Padia, J., et al., Filtration+Separation, 43 (2006) p. 28-31.

*Primary Examiner* — Amber R Orlando
*Assistant Examiner* — Britanny Precht
(74) *Attorney, Agent, or Firm* — Wood IP LLC (57) ABSTRACT

A gas exhaust filter device for a bioreactor with reduced blockage by condensed liquid is disclosed, which comprises a housing with a filter medium, a gas inlet and a gas outlet and also further comprises a plurality of ribs extending from at least one inner wall of the housing in a region between the gas inlet and the filter medium.

23 Claims, 6 Drawing Sheets

(56) References Cited

U.S. PATENT DOCUMENTS

| | | | | |
|---|---|---|---|---|
| 4,135,900 | A * | 1/1979 | Westlin | B01D 46/10 210/493.3 |
| 4,512,891 | A * | 4/1985 | Wright | B01D 29/012 156/202 |
| 5,000,768 | A * | 3/1991 | Hwang | F01N 3/0211 55/308 |
| 5,174,896 | A * | 12/1992 | Harms, II | B01D 29/111 210/455 |
| 5,531,892 | A * | 7/1996 | Duffy | B01D 29/012 210/493.1 |
| 5,783,086 | A * | 7/1998 | Scanlon | A47L 7/0042 210/416.1 |
| 5,800,586 | A * | 9/1998 | Cusick | B01D 39/202 210/491 |
| 5,810,898 | A * | 9/1998 | Miller | B01D 46/10 55/501 |
| 5,912,368 | A | 6/1999 | Satarino et al. | |
| 6,159,318 | A * | 12/2000 | Choi | B01D 29/012 156/167 |
| 6,328,442 | B1 * | 12/2001 | Brinkly | B41J 29/10 347/104 |
| 6,387,260 | B1 * | 5/2002 | Pimenov | B01J 47/024 210/282 |
| 6,936,086 | B2 * | 8/2005 | Harkonen | B01D 45/06 55/385.1 |
| 7,104,403 | B1 * | 9/2006 | Stephens | B07B 7/04 209/132 |
| 7,803,208 | B2 * | 9/2010 | Kawasaki | B01D 45/06 55/434 |
| 8,052,768 | B2 * | 11/2011 | Lin | F02M 25/089 55/320 |
| 8,132,559 | B2 * | 3/2012 | Dong | B01D 46/2411 123/519 |
| 2001/0015135 | A1 * | 8/2001 | Chybin | B01D 19/0063 96/165 |
| 2001/0025815 | A1 * | 10/2001 | Schwinghammer | B01D 46/10 210/348 |
| 2004/0077304 | A1 * | 4/2004 | Pfannenberg | F24F 13/28 454/184 |
| 2005/0161042 | A1 * | 7/2005 | Fudge | A61B 5/097 128/205.12 |
| 2010/0170400 | A1 | 7/2010 | Van Den Boogard et al. | |
| 2010/0224549 | A1 * | 9/2010 | Micke | B01D 29/356 210/321.65 |
| 2011/0076759 | A1 | 3/2011 | Reif et al. | |
| 2011/0207218 | A1 | 8/2011 | Stahell et al. | |
| 2012/0172800 | A1 * | 7/2012 | Dudar | A61M 5/36 604/123 |
| 2012/0261333 | A1 * | 10/2012 | Moran | B01D 63/10 210/500.23 |
| 2015/0157755 | A1 * | 6/2015 | Ellis | A61L 9/00 422/122 |

FOREIGN PATENT DOCUMENTS

| | | |
|---|---|---|
| JP | 3006908 U | 1/1995 |
| JP | 2003236323 A | 8/2003 |
| JP | 20050908657 A | 4/2005 |
| JP | 2008501347 A | 1/2008 |
| JP | 2008151130 A | 7/2008 |
| WO | 2011005773 A2 | 1/2011 |
| WO | 2011041508 A1 | 4/2011 |

* cited by examiner

GAS EXHAUST FILTER DEVICE FOR A BIOREACTOR

CROSS-REFERENCE TO RELATED APPLICATIONS

This application is a filing under 35 U.S.C. 371 of international application number PCT/SE2012/050912, filed Aug. 29, 2012, published on Mar. 7, 2013 as WO 2013/032392, which claims priority to application number 1150790-2 filed in Sweden on Aug. 31, 2011, the entire disclosure of each of which is hereby incorporated by reference.

TECHNICAL FIELD OF THE INVENTION

The present invention relates to bioreactors for cultivation of cells and in particular to gas exhaust filters for bioreactors. The invention also relates to cultivation of cells in bioreactors.

BACKGROUND OF THE INVENTION

During cultivation of cells in bioreactors, air and/or other gases are continuously supplied to the reactor and the excess, together with gaseous metabolites from the cells, is removed via an exhaust port. To ensure sterility of the culture, the exhaust line is equipped with a sterilisation grade filter, where the filter medium can typically be a 0.1-0.2 micron hydrophobic microfiltration membrane. Since the exhaust gas stream is warm and saturated with moisture, there is a significant risk that the moisture condenses on the filter medium, causing a blockage of the gas flow through the filter.

Several solutions have been described where a water-cooled condenser is placed in the exhaust line before the filter (U.S. Pat. No. 5,443,985; U.S. Pat. No. 6,133,021; U.S. Pat. No. 7,425,441) or integrated in the filter housing before the filter medium (US 2011/0076759). Any moisture is then condensed and the condensate can flow back to the bioreactor by gravity flow and thus avoiding any contact between liquid condensate and the filter medium. The use of a water-cooled condenser is however complicated in that water must be supplied via tubing, which must be thoroughly secured to the condenser and to a drain in order to avoid any leakage. Further, water-cooled condensers are complicated to manufacture in that double-walled vessels or vessels with internal tubing and tubing ports through the walls are needed. This is a drawback in particular for small to medium scale cell cultivation in disposable bioreactors, where it is highly desirable to use low cost disposable plastic components.

Hence, there is a need for a gas exhaust filter device which can be used in bioreactors without any liquid-cooled condensers.

SUMMARY OF THE INVENTION

One aspect of the invention is to provide a gas exhaust filter device for bioreactors, which is simple to manufacture and use and which does not require any liquid-cooled condenser. This is achieved with a gas exhaust filter device as defined in claim 1. One advantage of this construction is that it is amenable to low cost production as a single use device and that the device is easy to operate.

A second aspect of the invention is to provide a bioreactor with a single use gas exhaust filter device. This is achieved with a bioreactor as defined in claim 11. One advantage of this is that the absence of liquid coolant lines facilitates installation and assembly of the bioreactor.

A third aspect of the invention is to provide a convenient and reliable method for cell cultivation. This is achieved with a method as defined in claim 13. One advantage of this method is that blockage of the gas exhaust filter medium is avoided without the use of a liquid cooled condenser.

Further suitable embodiments of the invention are described in the depending claims.

DETAILED DESCRIPTION OF EMBODIMENTS

In a first aspect illustrated by FIGS. 1-5, the present invention discloses a gas exhaust filter device for a bioreactor which comprises a housing 2;12;22 with a filter medium 1, a gas inlet 3;13;23 and a gas outlet 4;14;24. The housing further comprises at least two ribs 5;15;25 extending from at least one inner wall of the housing 2;12;22 in a region between the gas inlet 3;13;23 and the filter medium 1. The filter medium can suitably extend across a section of the interior volume of the housing, delimiting two compartments—one between the gas inlet 3;13;23 and the filter medium 1 and one between the filter medium 1 and the gas outlet 4;14;24. The general direction of the filter medium 1 can be in a plane essentially perpendicular to, or at an angle of about 60-90 degrees relative to, a straight line drawn between the center of the gas inlet 3;13;23 and the center of the gas outlet 4;14;24. The ribs 5;15;25 can be integral with at least one wall of the housing or they can be separately manufactured and mounted in the housing. They can extend in a direction substantially perpendicular to at least one inner wall of the housing or they can be angled relative to an inner wall. An advantage of the ribs is that moisture in the air coming from a bioreactor can condense on the ribs and the condensate can flow back to the bioreactor by gravity.

Figure 1:
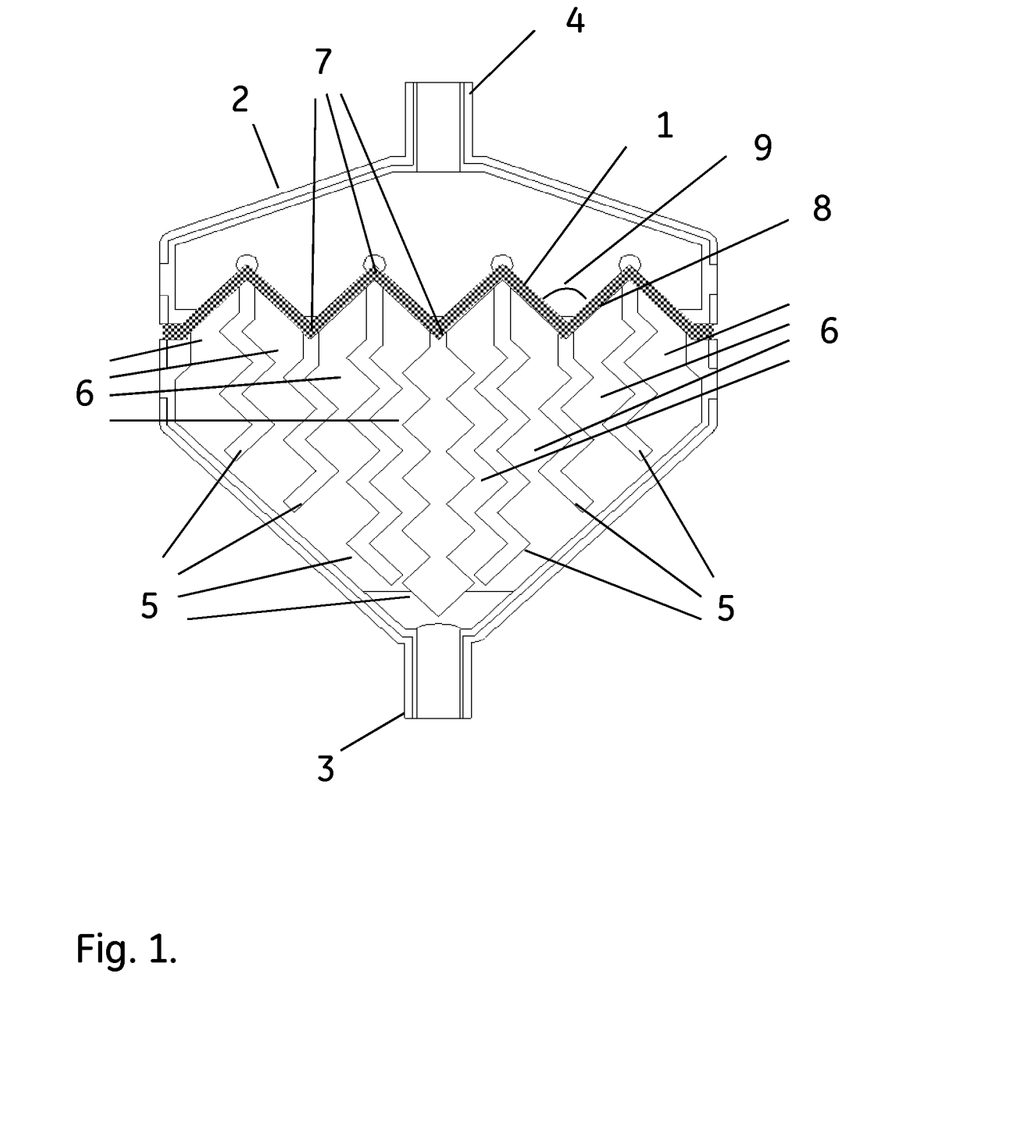
FIG. 1 shows a gas exhaust filter device according to the invention.
Figure 2:
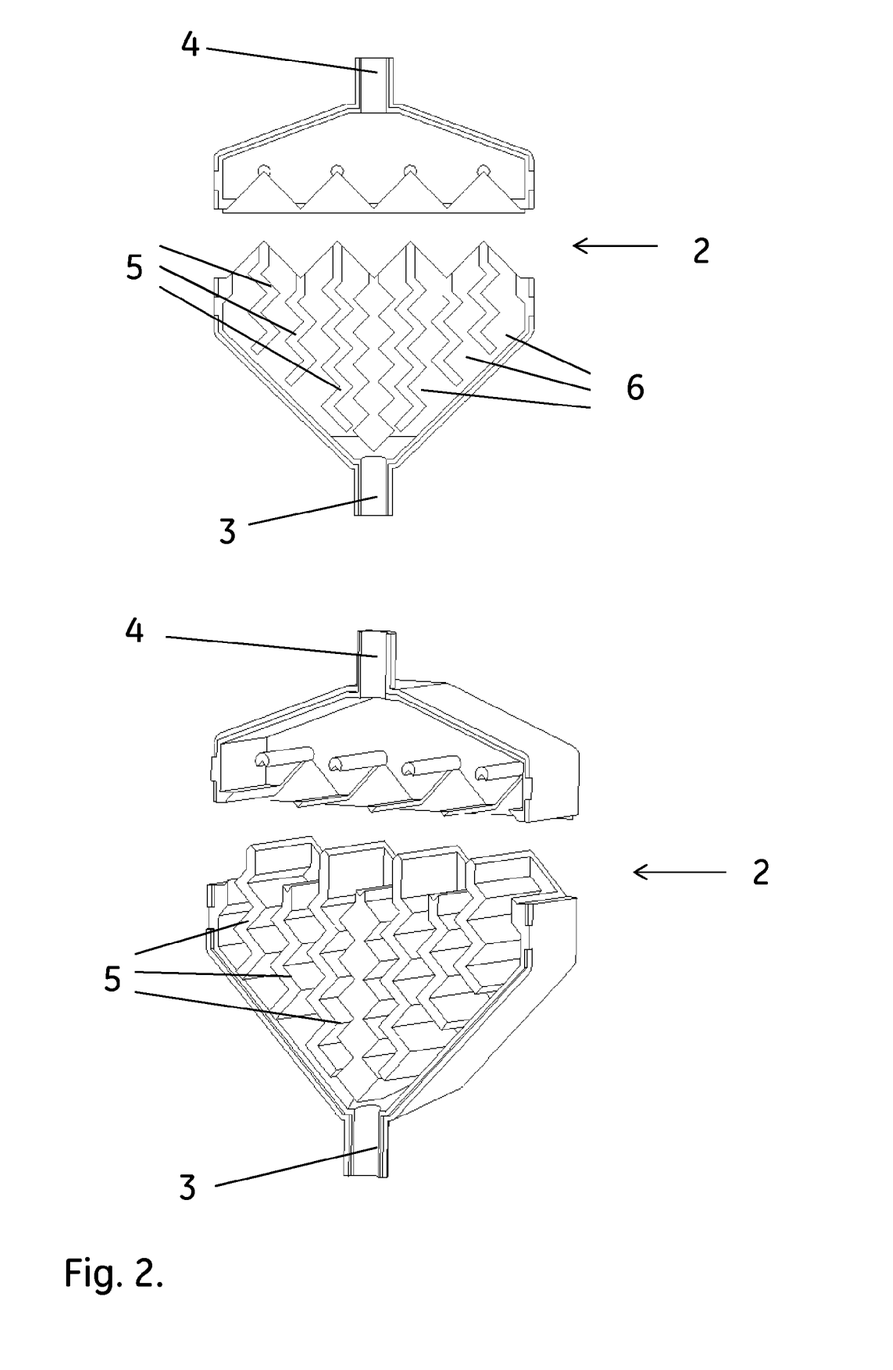
FIG. 2 shows parts of the housing for the gas exhaust filter device of FIG. 1.
Figure 3:
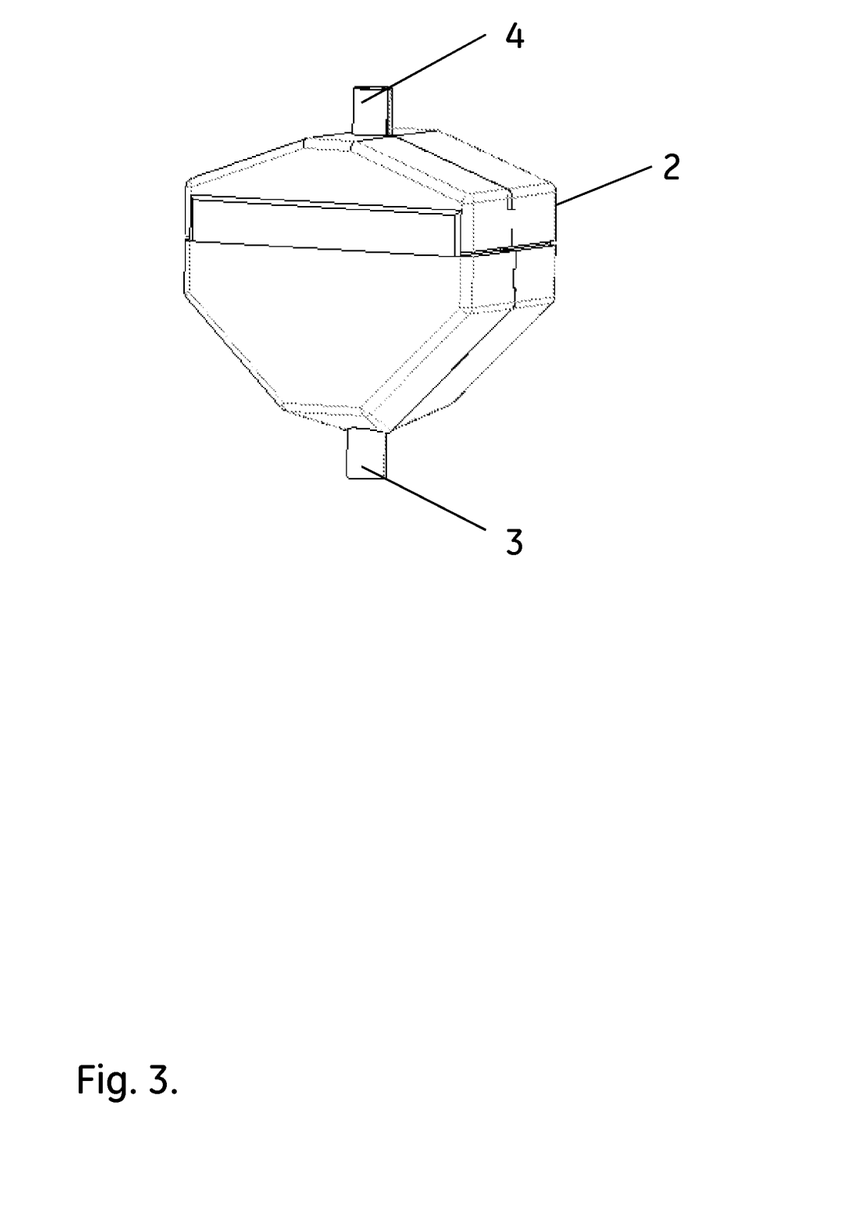
FIG. 3 shows a gas exhaust filter device according to the invention.
Figure 4:
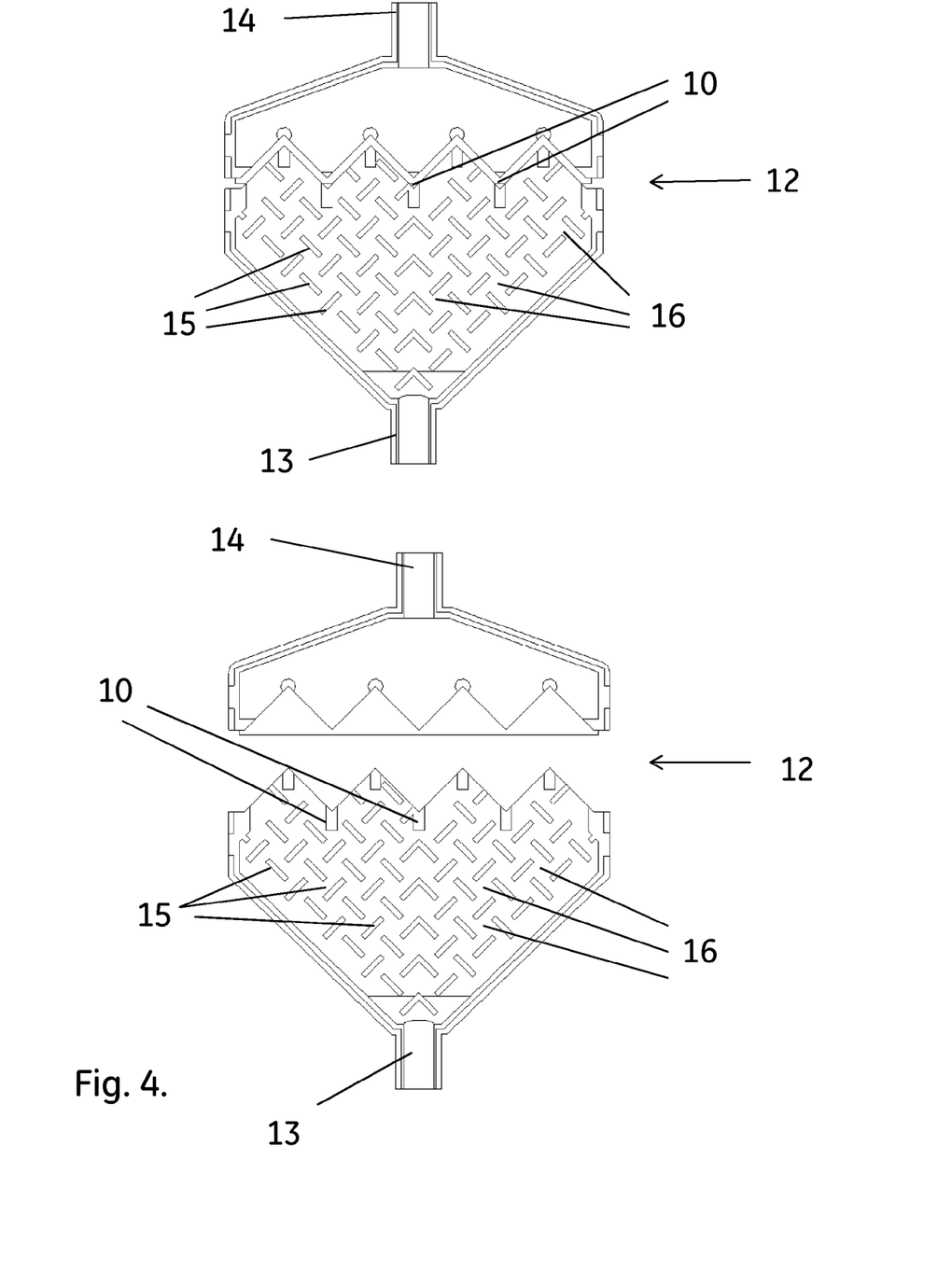
FIG. 4 shows parts of the housing for a gas exhaust filter device according to the invention.

In some embodiments, illustrated by FIGS. 1-5, the ribs extend between two opposite inner walls of said housing. They can then delimit a plurality of channels 6;16;26 between the bottom inlet and the filter medium 1, so that gas flow from the gas inlet 3;13;23 towards the filter medium 1 can be divided into several subflows. This increases the contact area between the gas and the rib surfaces and improves condensation. To further increase the contact area and thus improve condensation, the channels 6;16;26 can be tortuous, such as with an average tortuosity>1.1, where the tortuosity is defined as the length of a channel divided by the straight line end-to-end distance of the channel. The average tortuosity can be between 1.1 and 5, which can be achieved by having curved or angled ribs in the housing. The channels 6;26 can be parallel, as illustrated in FIGS. 1, 2 and 4, or they can form an interconnected network of channels 16, with branching and/or reconnection points as illustrated in FIG. 3.

In certain embodiments the ribs 5;15;25 are arranged in a continuous or discontinuous zigzag pattern. Continuous zigzag patterns are illustrated in FIGS. 1 and 2, where segments of a rib 5 are angled relative to each other in a regular pattern. Discontinuous zigzag patterns are illustrated in FIG. 3, where individual ribs 15 are angled relative to each other in a regular pattern. The angles in the zigzag patterns can e.g. be 60-120 degrees, such as 80-100 degrees. An advantage of using a zigzag pattern is that the gas flow is repeatedly deflected, leading to an improved contact with the rib surfaces and hence improved condensation.

In some embodiments the housing 2;12;22 is single-walled. Hence, there is no arrangement for supplying a liquid cooling medium to the gas exhaust filter device. A single-walled housing does not have any double walls formed either by design of the housing walls or by introducing a tubular circuit through the interior volume of the housing. An advantage of having a single walled housing is that it is easier to manufacture and install. A further advantage is also that heat transfer between the housing and ambient air is improved. The average thickness of the housing walls can be less than 1 mm, such as less than 0.5 mm to further improve the heat transfer with the surrounding air.

In certain embodiments the filter medium 1 is pleated to increase the filter area. The pleats 7 (alternatively called creases) can extend in a plane at an angle of 60-90 degrees, such as 80-90 degrees, relative to a straight line between the gas inlet 3;13;23 and the gas outlet 4;14;24. This means that when the gas exhaust filter device is operated more or less vertically, with the gas outlet at the top and the gas inlet at the bottom, the pleat legs 8 are angled relative to the horizontal plane and any moisture condensing in the filter can flow by gravity towards the lower pleats (creases), where the condensate can drip off the pleats (creases) and flow back to the bioreactor by gravity.

In some embodiments the pleat angle 9 of the pleated filter medium is 20-120 degrees, such as 30-100 degrees. A pleat angle below 120 or 100 degrees ensures the gravity flow of any condensate towards the lower pleats as described above and it also allows for a significant increase of the filter medium area. Below 20 or 30 degrees pleat angle there is a risk that any condensate can form water bridges between the pleat legs 8, which can lead to blockage of part of the filter medium area.

In certain embodiments a plurality of pleats (creases), such as all the lower pleats (the pleats/creases facing the gas inlet), are supported by pleat support rods 10;20 extending from at least one wall of the housing 12;22. The pleat support rods can have angular recesses fitting the pleats. One advantage of the pleat support rods is that the mounting of the filter medium is facilitated and that the mechanical stability is improved. Another advantage is that the pleat support rods can facilitate the dripping of condensed moisture from the lower pleats/creases. In some embodiments the filter medium is hydrophobic. A hydrophobic filter medium is not wetted by pure water but allows passage of gases. The hydrophobic character can be assessed by a water penetration test, where pure water is forced through the filter medium by an applied pressure and the pressure needed for water penetration is noted. A 0.20 micron filter medium can be denoted as hydrophobic if the water penetration pressure is above about 1 bar (100 kPa), such as above about 3 bar. An advantage of using a hydrophobic filter is that aerosol droplets entrained in the gas flow do not pass the filter. Hydrophobic filters are also less prone to blocking by condensation of moisture. The pore size of the filter can be chosen to ensure sterility of the bioreactor content. This is typically done with sterilization grade filters having a pore size below about 0.25 microns, such as 0.05-0.20 microns or 0.1-0.22 microns.

The surfaces of the ribs and the interior walls of the housing can in some embodiments be hydrophilic, such as with an equilibrium water contact angle of less than 50 degrees, to facilitate condensation and drainage of any moisture. The hydrophilicity may be achieved by treatments such as corona or plasma treatment, or by coating the surfaces with a hydrophilic material.

In certain embodiments the gas exhaust filter device further comprises at least one Peltier element clamped to an outer wall of the housing and/or means for clamping at least one Peltier element to an outer wall of the housing. An advantage of clamping Peltier elements to the housing is that an increased rate of condensation can be achieved without applying any liquid coolant.

Figure 6:
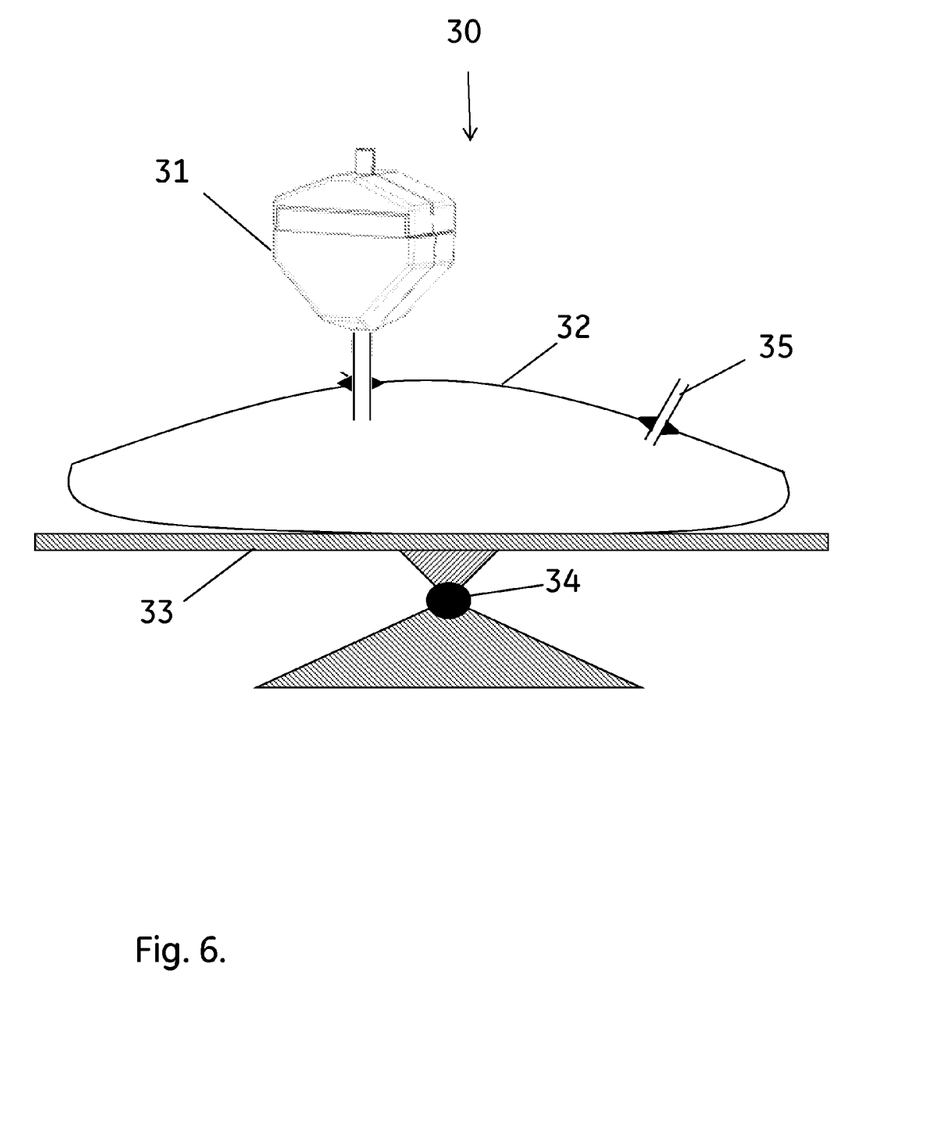
FIG. 6 shows a bioreactor with a gas exhaust filter device according to the invention.

In a second aspect, illustrated by FIG. 6, the invention discloses a bioreactor 30 equipped with a gas exhaust filter device 31 as described above. The bioreactor can be a disposable bioreactor and may comprise a flexible plastic bag 32 as the bioreactor vessel and a bioreactor gas inlet 35. Both the gas exhaust filter device and the gas inlet may be mounted in ports in the top wall of the flexible plastic bag. Such a flexible plastic bag can be mounted on a movable platform 33 which provides agitation by e.g. rocking motion around a pivoting axis 34. A particular advantage of using the described gas exhaust filter device with a rocking flexible bag bioreactor is that the absence of any liquid coolant tubing facilitates the setup and operation of the bioreactor in that no rocking tubing is needed. Flexible bag bioreactors are also normally used with only disposable components, emphasizing the need for a gas exhaust filter device with low production cost. The bag 32, the filter device 31, tubing and other disposable components may be supplied as a preassembled set, which may be sterilized e.g. by exposure to gamma or electron beam radiation. It is then advantageous if all the components, including the gas exhaust filter device, are manufactured from radiation-resistant materials, i.e. materials that do not degrade significantly upon exposure to 25 kGy radiation dose and that do not produce undesirable leachables after irradiation.

In a third aspect, illustrated by FIG. 6, the invention discloses a method for cultivation of cells in a bioreactor equipped with a gas exhaust filter device as described above.

In certain embodiments moisture from the bioreactor enters the gas exhaust filter device and condenses on the plurality of ribs during cultivation.

In some embodiments the cell suspension volume (the liquid volume) is less than 100 L, such as between 0.5 L and 20 L. In small to medium size cultures, the amount of moisture carried off from the bioreactor is such that it can easily be handled with one gas exhaust filter device as described above. For larger cultures, several devices may be needed. The gas flow rate through the gas exhaust filter device may be less than 2 L/min, such as between 0.05 and 1 L/min. If several gas exhaust filter devices are used, the flow rate in each device may be less than 2 L/min, such as between 0.05 and 1 L/min.

In certain embodiments no cooling liquid is applied to said gas exhaust filter device. This simplifies the operation.

In some embodiments the gas exhaust filter device is positioned with the gas outlet 4;14;24 above the gas inlet 3;13;23 and with a straight line between said gas inlet and said gas outlet at less than about 30 degrees relative to a vertical plane. This generally vertical orientation of the gas exhaust filter device facilitates the gravity flow of condensed moisture from the ribs and/or the pleats/creases and back to the bioreactor.

EXAMPLES

Example 1

Test Equipment:

A WAVE Bioreactor System 2/10 instrument (GE Healthcare Bio-Sciences, Sweden), five 2 L Cellbag™ flexible bags (GE Healthcare Bio-Sciences, Sweden), each filled with 1 L NaCl 9 mg/ml and equipped with an air inlet an a gas exhaust filter device in the gas outlet. The parameter settings for the Wave instrument were:

| Temperature | 37.2° C. |
| Rocking rate | 10 rpm |
| Rocking angle | 6° |
| Air Flow | 0.21 L/min |
| Time | 23 hours |

The dry filter devices were weighed at start and again after the 23 h run in the Wave instrument.

The weight of the condensate was compared with the weight from the reference set up with the standard gas exhaust filter supplied with the bag, having a flat filter medium and no ribs. Two filter device prototypes were evaluated, one according to FIG. 5 and one according to FIG. 4. The results are shown in Table 1.

TABLE 1

Figure 5:
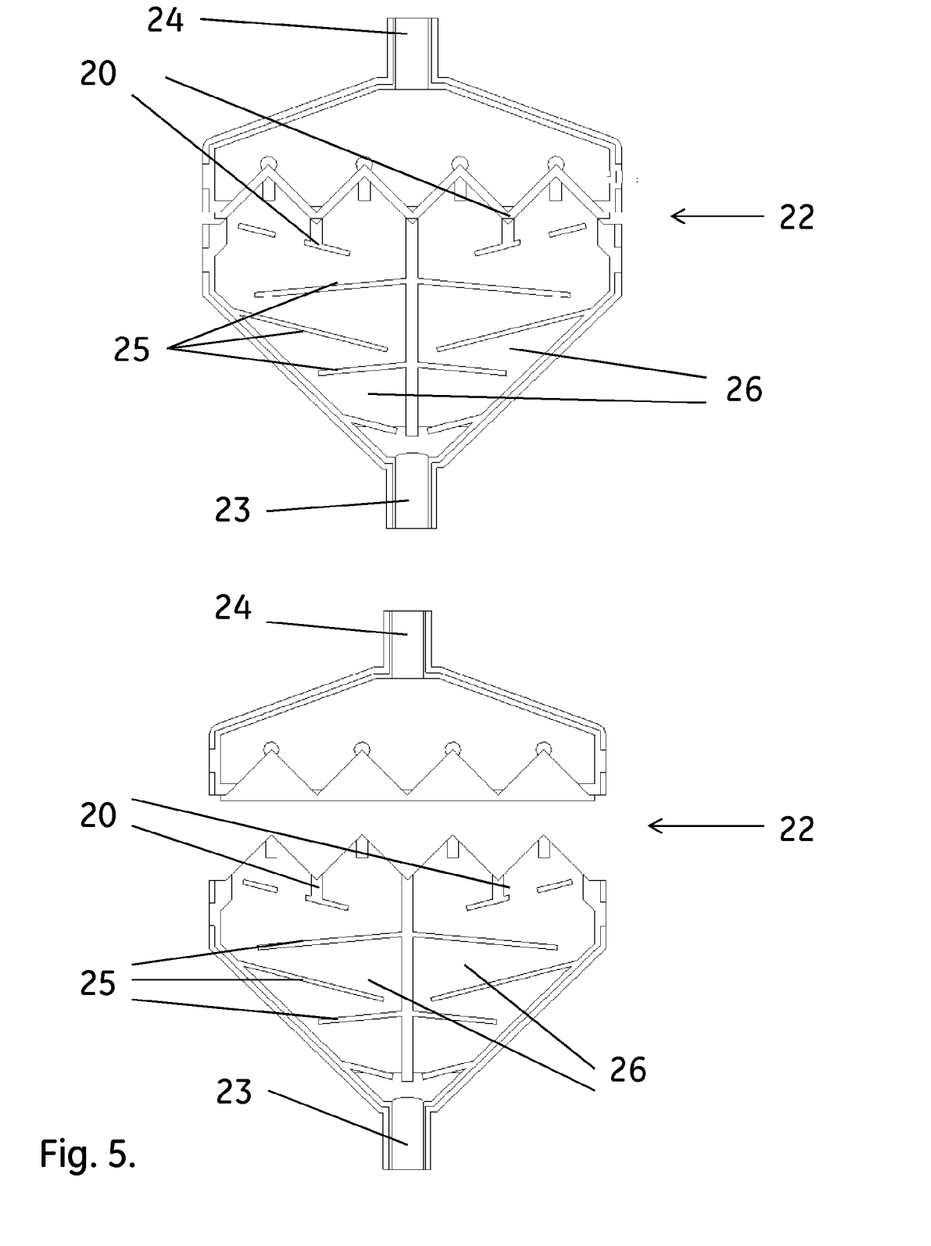
FIG. 5 shows parts of the housing for a gas exhaust filter device according to the invention.

| Filter device | Time (h) | Liquid in filter (g) |
|---|---|---|
| Reference | 23 | 2.21 |
| FIG. 5 prototype | 23 | 0.10 |
| FIG. 5 prototype | 23 | 0.12 |
| FIG. 4 prototype | 23 | 0.36 |
| FIG. 4 prototype | 23 | 0.20 |

It is evident that the amount of condensate remaining in the filter is strongly reduced by the new constructions.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. It is pointed out that any feature described in relation to one embodiment may be used also in combination with one or more features of any other of the embodiments described.

The invention claimed is:

1. A gas exhaust filter device for filtering moisture containing exhaust gas of a bioreactor, the filer device comprising a housing with a filter medium, a gas inlet, a gas outlet, and a plurality of ribs extending from at least one inner wall of said housing in a region between the gas inlet and the filter medium,
wherein the filter medium is pleated with the pleats extending in a plane at an angle of 60-90 degrees relative to a straight line between said gas inlet and said gas outlet, and
wherein the surface of the ribs and the interior walls of the housing is hydrophilic and the filter medium is hydrophobic.

2. The gas exhaust filter device of claim 1, wherein said ribs extend between two opposite inner walls of said housing, delimiting a plurality of tortuous channels between the gas inlet and the filter medium.

3. The gas exhaust filter device of claim 1, wherein said ribs are arranged in a continuous or discontinuous zigzag pattern.

4. The gas exhaust filter device of claim 1, wherein the housing is single-walled and the thickness of the housing wall is less than 1 mm.

5. The gas exhaust filter device of claim 1, wherein the pleats are extending in a plane at an angle of 80-90 degrees relative to a straight line between said gas inlet and said gas outlet.

6. The gas exhaust filter device of claim 5, wherein the pleat angle is 20-120 degrees.

7. The gas exhaust filter device of claim 5, wherein a plurality of pleats are supported by pleat support rods extending from at least one wall of the housing.

8. The gas exhaust filter device of claim 1, further comprising at least one Peltier element clamped to an outer wall of the housing.

9. A bioreactor set that comprises a bioreactor equipped with at least one gas exhaust filter device of claim 1.

10. The bioreactor set of claim 9, wherein the bioreactor comprises a flexible bag.

11. A method for cultivation of cells in a bioreactor set according to claim 9.

12. The method of claim 11, wherein moisture condenses on the plurality of ribs during cultivation.

13. The method of claim 11, wherein the cell culture volume is less than 100 L.

14. The method of claim 11, wherein no cooling liquid is applied to said gas exhaust filter device.

15. The method of claim 11, wherein the gas exhaust filter device is positioned with the gas outlet above the gas inlet and with a straight line between said gas inlet and said gas outlet at less than about 30 degrees relative to a vertical plane.

16. The bioreactor set of claim 9, wherein the bioreactor is a flexible bag that can be mounted on a movable platform that provides agitation.

17. The method of claim 11, wherein the cell culture volume is between 0.5 L and 20 L.

18. A gas exhaust filter device for a bioreactor, comprising a housing with a filter medium, a gas inlet a gas outlet, and a plurality of ribs extending from at least one inner wall of said housing in a region between the gas inlet and the filter medium and wherein the surface of the ribs and the interior walls of the housing is hydrophilic and the filter medium is hydrophobic,
wherein the filter medium is pleated with the pleats extending in a plane at an angle of 60-90 degrees relative to a straight line between said gas inlet and said gas outlet,
wherein said ribs extend between two opposite inner walls of said housing, delimiting a plurality of tortuous channels between the gas inlet and the filter medium,
wherein said ribs are arranged in a continuous or discontinuous zigzag pattern, and wherein at least a portion of the housing is conical cylindrical in shape.

19. The filter device of claim 1, wherein the filter is sterilization grade and the filter medium is a 0.1-0.2 micron hydrophobic microfiltration membrane.

20. The filter device of claim 1, wherein the filter device is disposable.

21. The filter device of claim 1, wherein the exhaust gas flow rate through the filter device is less than 2 L/min.

22. The bioreactor set of claim 9, wherein the bioreactor set is disposable.

23. The bioreactor set of claim 9, wherein the bioreactor set is made from radiation resistant material.

* * * * *